US012722487B2

(12) United States Patent
Pang et al.

(10) Patent No.: US 12,722,487 B2
(45) Date of Patent: Sep. 1, 2026

(54) SYSTEM AND METHOD TO LEAVE A MESSAGE OR COMMUNICATE WITH SOMEONE OUTSIDE OF A VEHICLE

(71) Applicant: GM Global Technology Operations LLC, Detroit, MI (US)

(72) Inventors: Janghyuk Pang, Incheon (KR); Jaehyun Hwang, Bupyeong-gu (KR); Hyungsuk Noh, Yeonsu-gu (KR); Sngjin Lee, Incheon (KR); Gaurav Talwar, Novi, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 18/809,558

(22) Filed: Aug. 20, 2024

(65) Prior Publication Data

US 2026/0054570 A1 Feb. 26, 2026

(51) Int. Cl.

| | |
|---|---|
| ***B60K 35/28*** | (2024.01) |
| ***B60K 35/23*** | (2024.01) |
| ***B60W 40/08*** | (2012.01) |
| ***B60W 60/00*** | (2020.01) |
| ***G16H 10/60*** | (2018.01) |

(52) U.S. Cl.

CPC .............. *B60K 35/28* (2024.01); *B60K 35/23* (2024.01); *B60W 40/08* (2013.01); *B60W 60/0015* (2020.02); *G16H 10/60* (2018.01); *B60K 2360/148* (2024.01); *B60K 2360/566* (2024.01); *B60K 2360/785* (2024.01); *B60W 2540/221* (2020.02); *B60W 2556/45* (2020.02)

(58) Field of Classification Search

CPC .. B60K 35/28; B60K 35/23; B60K 2360/148; B60K 2360/566; B60K 2360/785; B60W 40/08; B60W 60/0015; B60W 2540/221; B60W 2556/45; G16H 10/60

See application file for complete search history.

(56) References Cited

U.S. PATENT DOCUMENTS

| | | | | |
|---|---|---|---|---|
| 6,304,174 | B1 * | 10/2001 | Smith | B60Q 1/5035 340/471 |
| 2012/0050028 | A1 * | 3/2012 | Mastronardi | H04W 4/12 340/425.5 |
| 2015/0180999 | A1 * | 6/2015 | Pisz | B60K 35/81 709/204 |
| 2016/0042627 | A1 * | 2/2016 | Foley | G08B 21/06 340/576 |
| 2017/0322558 | A1 * | 11/2017 | Teshima | H04L 67/00 |
| 2019/0318609 | A1 * | 10/2019 | Obayuwana | B60Q 5/005 |
| 2020/0101977 | A1 * | 4/2020 | Nakai | G05D 1/0061 |
| 2020/0193878 | A1 * | 6/2020 | Shepard | G09F 13/0413 |
| 2022/0074758 | A1 * | 3/2022 | Sameer | G06N 20/10 |

(Continued)

*Primary Examiner* — Ryan W Sherwin
(74) *Attorney, Agent, or Firm* — Honigman LLP; Matthew H. Szalach

(57) ABSTRACT

A system and method include detecting that a status of a vehicle indicates that the vehicle is parked, receiving context data of a user of the vehicle, and generating a message for display via a window of the vehicle, the message directed to external users outside of the vehicle. The system and method also include displaying the message on a user device in communication with the data processing hardware, receiving a user indication indicating approval of the message, and displaying, via the window of the vehicle, the message to the external users outside of the vehicle.

20 Claims, 7 Drawing Sheets

(56) References Cited

U.S. PATENT DOCUMENTS

2022/0076670 A1* 3/2022 Marti .................... G01S 15/931
2022/0219535 A1* 7/2022 Kim ...................... B60W 50/14
2022/0410709 A1* 12/2022 Florentz ............. B60R 11/0235

* cited by examiner

SYSTEM AND METHOD TO LEAVE A MESSAGE OR COMMUNICATE WITH SOMEONE OUTSIDE OF A VEHICLE

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates generally to a system and method of leaving a message or communicating with someone outside of a vehicle. Generally, systems for a user of a vehicle to communicate with external parties is limited to in-person interaction. For example, a driver may honk the horn or turn on the emergency lights of the vehicle to communicate with external parties. Moreover, in instances where the driver is remote from the parked vehicle, the primary method of communicating with external parties is via pen and paper. However, these methods do not allow for filtering messages to more quickly reach the remote user based on the urgency of the message, which is of particular importance when an accident has occurred. As such, it is of particular interest to improve communications between the driver and external parties when the situation calls for immediate communication or the vehicle and/or the driver are in danger.

SUMMARY

One aspect of the disclosure provides a computer-implemented method for leaving a message or communicating with someone outside of a vehicle that when executed on data processing hardware causes the data processing hardware to perform operations that include detecting that a status of a vehicle indicates that the vehicle is parked, receiving context data of a user of the vehicle, and generating a message for display via a window of the vehicle, the message directed to external users outside of the vehicle. The operations also include displaying the message on a user device in communication with the data processing hardware, receiving a user indication indicating approval of the message for display via the window of the vehicle, and displaying, via the window of the vehicle, the message to the external users outside of the vehicle.

Implementations of the disclosure may include one or more of the following optional features. In some implementations, generating the message for display via the window includes retrieving a predefined message from a message data store based on the context data of the user of the vehicle. In some examples, the operations further include receiving a user defined message. In these examples, generating the message for display via the window of the vehicle may include re-formatting the user defined message as the message.

In some implementations, the operations further include detecting that an external user is within a threshold distance of the vehicle, prompting, via the window, the external user to leave a message for the user of the vehicle, receiving audio data corresponding to an utterance spoken by the external user, and generating, based on the audio data, an external user message. In these implementations, the operations may further include transmitting the external user message to the user of the vehicle. In some examples, displaying, via the window of the vehicle, the message to the external users outside of the vehicle includes projecting the message via a head-up display of the vehicle.

Another aspect of the disclosure provides a computer-implemented method for communicating a medical emergency to someone outside of a vehicle that when executed on data processing hardware causes the data processing hardware to perform operations that include receiving user data measured by a health monitoring system of a vehicle, and detecting, based on the user data, that a user of the vehicle is experiencing a medical emergency. The operations also include generating a message for display via a window of the vehicle, the message communicating the medical emergency to external users outside of the vehicle, and displaying, via the window of the vehicle, the message to the external users outside of the vehicle.

This aspect may include one or more of the following optional features. In some implementations, the user data includes one or more of pulse rate beats per minute, temperature, posture, oxygen levels, or eye movement. In some examples, detecting that the user of the vehicle is experiencing the medical emergency may be further based on health records of the user.

Another aspect of the disclosure provides a system for leaving a message or communicating with someone outside of a vehicle that includes data processing hardware and memory hardware in communication with the data processing hardware. The memory hardware stores instructions that when executed by the data processing hardware cause the data processing hardware to perform operations that include detecting that a status of a vehicle indicates that the vehicle is parked, receiving context data of a user of the vehicle, and generating a message for display via a window of the vehicle, the message directed to external users outside of the vehicle. The operations also include displaying the message on a user device in communication with the data processing hardware, receiving a user indication indicating approval of the message for display via the window of the vehicle, and displaying, via the window of the vehicle, the message to the external users outside of the vehicle.

This aspect may include one or more of the following optional features. In some implementations, generating the message for display via the window includes retrieving a predefined message from a message data store based on the context data of the user of the vehicle. In some examples, the operations further include receiving a user defined message. In these examples, generating the message for display via the window of the vehicle may include re-formatting the user defined message as the message.

In some implementations, the operations further include detecting that an external user is within a threshold distance of the vehicle, prompting, via the window, the external user to leave a message for the user of the vehicle, receiving audio data corresponding to an utterance spoken by the external user, and generating, based on the audio data, an external user message. In these implementations, the operations may further include transmitting the external user message to the user of the vehicle. In some examples, displaying, via the window of the vehicle, the message to the external users outside of the vehicle includes projecting the message via a head-up display of the vehicle.

In some implementations, the operations further include receiving user data measured by a health monitoring system of a vehicle, detecting, based on the user data, that a user of the vehicle is experiencing a medical emergency, generating a message for display via a window of the vehicle, the message communicating the medical emergency to external users outside of the vehicle, and displaying, via the window of the vehicle, the message to the external users outside of the vehicle. In these implementations, detecting that the user of the vehicle is experiencing the medical emergency may be further based on health records of the user.

The details of one or more implementations of the disclosure are set forth in the accompanying drawings and the description below. Other aspects, features, and advantages will be apparent from the description and drawings, and from the claims.

BRIEF DESCRIPTION OF THE DRAWINGS

The drawings described herein are for illustrative purposes only of selected configurations and are not intended to limit the scope of the present disclosure.

Corresponding reference numerals indicate corresponding parts throughout the drawings.

DETAILED DESCRIPTION

Figure 1:
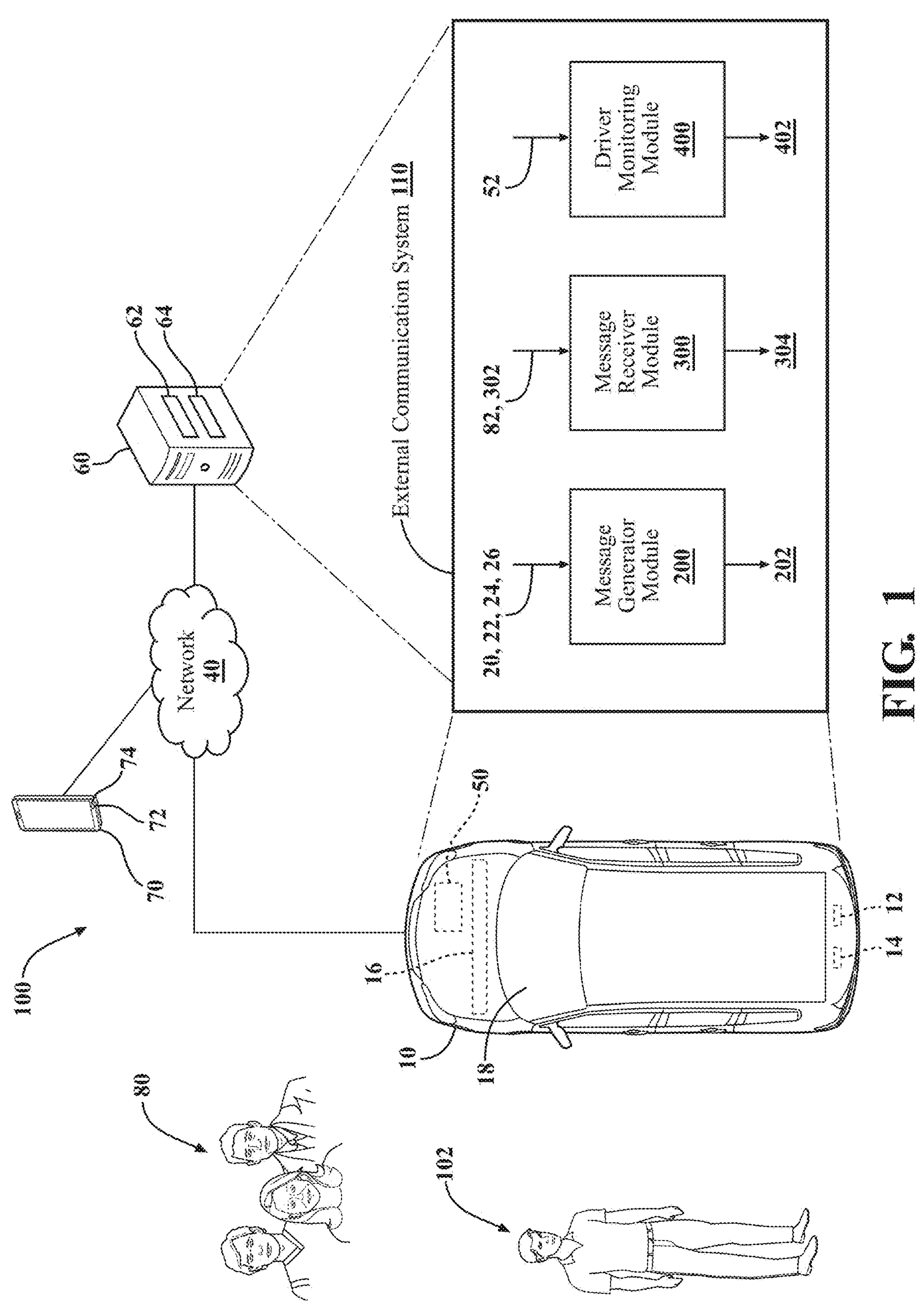
FIG. 1 is a schematic view of an example system for leaving a message or communicating with someone outside of a vehicle.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms "first," "second," "third," etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

In this application, including the definitions below, the term "module" may be replaced with the term "circuit." The term "module" may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term "code," as used above, may include software, firmware, and/or microcode, and may refer to programs, routines, functions, classes, and/or objects. The term "shared processor" encompasses a single processor that executes some or all code from multiple modules. The term "group processor" encompasses a processor that, in combination with additional processors, executes some or all code from one or more modules. The term "shared memory" encompasses a single memory that stores some or all code from multiple modules. The term "group memory" encompasses a memory that, in combination with additional memories, stores some or all code from one or more modules. The term "memory" may be a subset of the term "computer-readable medium." The term "computer-readable medium" does not encompass transitory electrical and electromagnetic signals propagating through a medium, and may therefore be considered tangible and non-transitory memory. Non-limiting examples of a non-transitory memory include a tangible computer readable medium including a nonvolatile memory, magnetic storage, and optical storage.

The apparatuses and methods described in this application may be partially or fully implemented by one or more computer programs executed by one or more processors.

The computer programs include processor-executable instructions that are stored on at least one non-transitory tangible computer readable medium. The computer programs may also include and/or rely on stored data.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Referring to FIG. 1, in some implementations, a system 100 includes a vehicle 10, a user device 70, and/or a remote system 60 in communication with one another via a network 40 (e.g., wired or wireless communication). The vehicle 10, the user device 70, and/or the remote system 60 execute an external communication system 110. Briefly, and as described in further detail below, the external communication system 110 is configured to facilitate communication between a user 102 of the vehicle 10 and external users 80 located outside of the vehicle 10. For example, when the vehicle 10 is parked, the external communication system 110 is configured to generate a message 202 approved by the user 102 and for display via a window 18 of the vehicle 10. Notably, the external communication system 110 may further be used by the external users 80 to leave a message for the user 102 of the vehicle 10, or to communicate with external users 80 when the user 102 of the vehicle 10 is experiencing a medical emergency. By allowing the user 102 and/or the external users 80 to leave or communicate any message, the external communication system 110 may facilitate communications that are otherwise limited during emergencies (e.g., fender benders and/or collisions) or time-sensitive situations (e.g., how long a car will be parked).

In the example shown, the external communication system 110 is implemented within the vehicle 10. However, the external communication system 110 can be implemented in any other propulsion system, such as, without limitation, motorcycles, trucks, off-road vehicles, farm equipment, trains, aircraft, and the like. The vehicle 10 includes data processing hardware 12 and memory hardware 14 storing instructions that when executed on the data processing hardware 12 cause the data processing hardware 12 to perform operations. The vehicle 10 further includes a head-up display 16 configured to display, via the window 18 of the vehicle 10, messages 202 and/or prompts 322 (FIG. 5B). The head-up display 16 may project the message 202 directly onto the window 18 such that the message 202 is readable to an external user 80 disposed outside of the vehicle 10. Optionally, the head-up display 16 includes a message film plate configured to collect emitted light conveying the message 202. Additionally or alternatively, the head-up display 16 includes an electronic paper (e-paper) configured to display the message 202. While the window 18 shown in FIG. 1 is disposed on the windshield of the vehicle 10, it should be appreciated that the head-up display 16 may display the message 202 via any windows of the vehicle 10, such as the rear window, the passenger windows, and/or the driver window.

The remote system 60 (e.g., server, cloud computing environment) also includes data processing hardware 62 and memory hardware 64 storing instructions that when executed on the data processing hardware 62 cause the data processing hardware 62 to perform operations. Additionally, as shown, the system 100 includes the user device 70 (e.g., a mobile device of the user 102). The user device 70 also includes data processing hardware 72 and memory hardware 74 storing instructions that when executed on the data processing hardware 72 cause the data processing hardware 72 to perform operations. An assistant application (not shown) executing on the user device 70 may facilitate communication with the remote system 60 and the vehicle 10. In some examples, execution of the external communication system 110 is shared across the vehicle 10, the user device 70, and/or the remote system 60.

As shown, the external communication system 110 includes a message generator module 200, a message receiver module 300, and a driver monitoring module 400. The message generator module 200 is configured to generate and display messages 202 from the user 102 that are directed to external users 80 outside of the vehicle 10. The message receiver module 300 is configured to detect when external users 80 are near the vehicle 10, and record a message from the external user 80 for the user 102 of the vehicle 10. The driver monitoring module 400 is configured to monitor the health of the user 102 of the vehicle 10, and communicate medical emergencies that that the user 102 of the vehicle 10 is experiencing.

Figure 2:
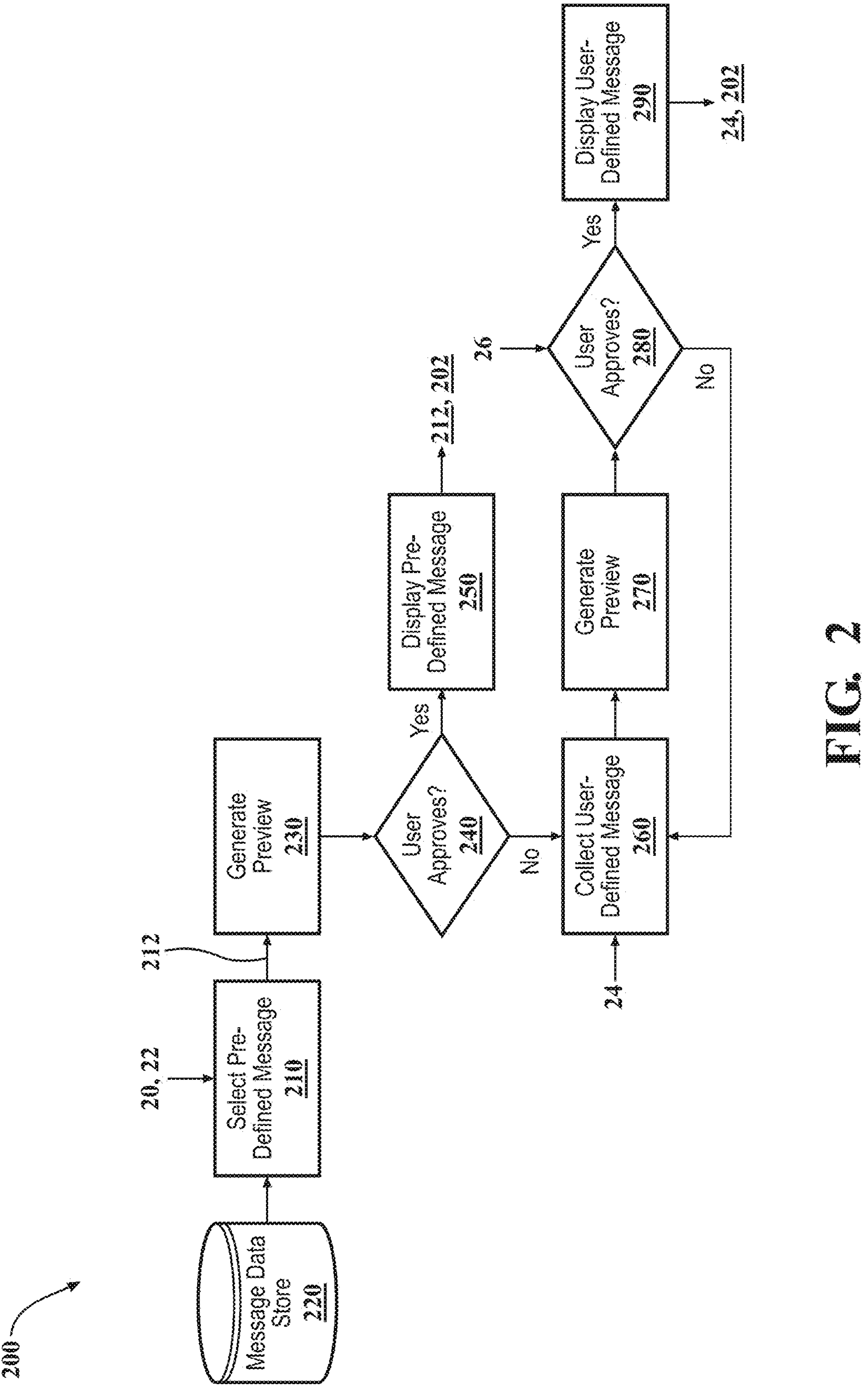
FIG. 2 is a message generator module flowchart for the system of FIG. 1.

With reference to FIGS. 1 and 2, the message generator module 200 is configured to execute when the vehicle 10 is parked. In particular, the message generator module 200 continually monitors the status 20 of the vehicle 10, and when the vehicle 10 detects that the status 20 of the vehicle 10 indicates that the vehicle 10 is parked, the message generator module 200 is configured to receive, context data 22 of the user 102 of the vehicle 10. As used herein, the context data 22 of the user 102 may generally refer to profile information of the user 102, a location of the user 102, a calendar of the user 102, routines of the user 102, historical movement data of the user 102, etc. In some implementations, the message generator module 200 has access to a message data store 220 that records/stores pre-defined messages 212 as well as historical context data 22 of the user 102. The pre-defined messages 212 and/or the historical context data 22 of the user 102 may be stored on any one of the memory hardware 14, 64, 74. The pre-defined messages 212 may be pre-loaded by a manufacturer of the vehicle 10, and/or may include previously displayed messages 202 used by the user 102. Here, during operation 210, the message generator module 200 may query the message data store 220 and select a pre-defined message 212 to display via the window 18 of the vehicle 10. In some implementations, the pre-defined message 212 is selected based on the context data 22 of the user 102. For example, the pre-defined message 212 may include "be right back," when the context data 22 indicates that the user 102 and the vehicle 10 are parked at a coffee shop that the user 102 visits for short periods of time. In other examples, the pre-defined message may include "please contact Security at 248-999-9999" when the context data 22 indicates that the user 102 is attending a meeting at a location including a security team.

At operation 230, the message generator module 200 may generate a preview of the pre-defined message 212. For example, the message generator module 200 may generate the pre-defined message 212 as the message 202 for display on an infotainment center (not shown) of the vehicle 10, and/or on a screen of the user device 70. At operation 240, the message generator module 200 may determine whether the user 102 approves of the pre-defined message 212. If the user 102 approves of the pre-defined message 212, the message generator module 200 may generate, as output, the pre-defined message 212 as the message 202 displayed via the window 18 of the vehicle 10. When the message 202 is displayed via the window 18 of the vehicle 10, an external user 80 passing near the vehicle 10 may view the message 202 and take action based on the message when relevant to that particular external user 80.

In contrast, when the user does not approve of the pre-defined message 212, the message generator module 200 may, at operation 260, collect a user-defined message 24 from the user 102. For example, the assistant application executing on the user device 70 may prompt the user 102 to provide (e.g., via any one or of touch, speech, gesture, gaze, and/or an input device (e.g., mouse or stylus)) the user-defined message 24. Thereafter, at operation 270, the message generator module 200 may generate a preview of the user-defined message 24. For example, the message generator module 200 may generate the user-defined message 24 as the message 202 for display on the infotainment center of the vehicle 10 and/or on the screen of the user device 70. If, at operation 280, the user 102 does not approve of the preview of the message 202 based on the user-defined message 24, then the message generator module 200 may re-prompt the user 102 to provide modifications to the message 202. Conversely, if, at operation 280, the user 102 approves of the message 202 (e.g., via a user indication 26), then at operation 290, the message generator module 200 generates, as output, the user-defined message 24 as the message 202 displayed via the window 18 of the vehicle 10.

Figure 3:
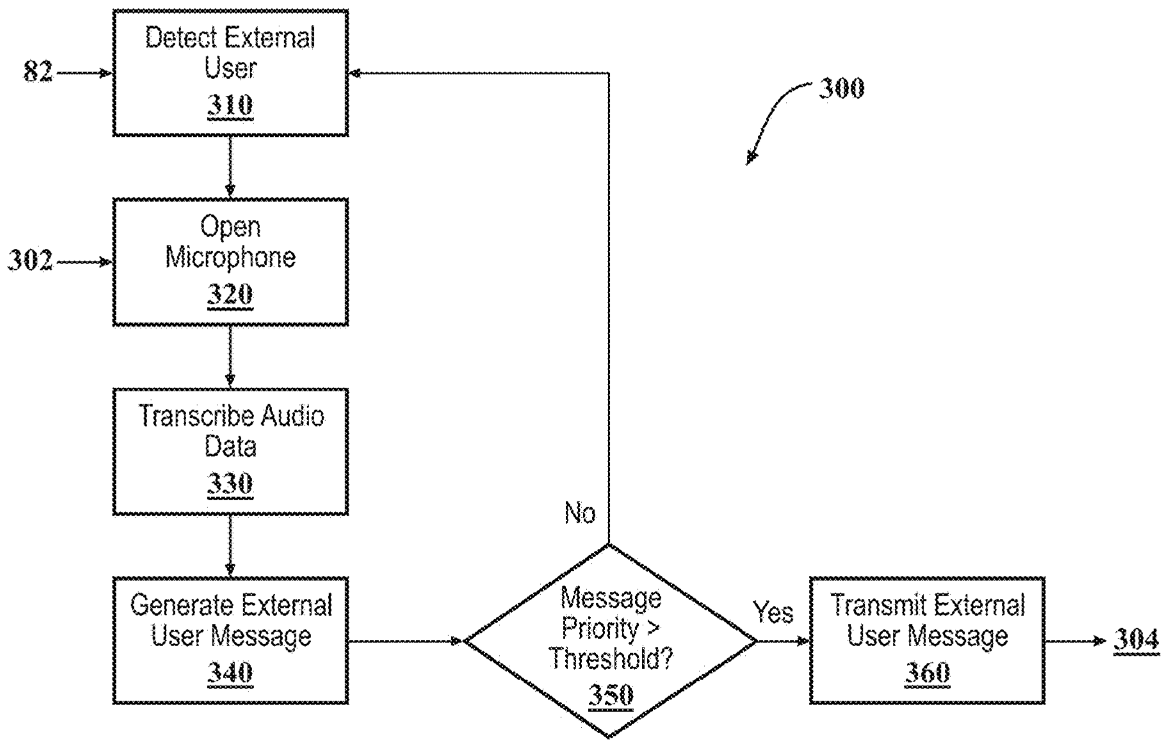
FIG. 3 is a message receiver module flowchart for the system of FIG. 1.

Referring to FIGS. 1 and 3, the message receiver module 300 is shown. The message receiver module 300 is configured to detect an external user 80 and receive a message from the external user 80 for the user 102 of the vehicle 10. At operation 310, the message receiver module 300 may detect an external user 80 within a threshold distance of the vehicle 10. For example, the message receiver module 300 may execute a passive infrared sensor (PIR) microsearch that detects, in sensor data 82, whether a keyfob and/or digital keypass is close to the vehicle 10. Here, when the message receiver module detects the external user 80 within the threshold distance of the vehicle 10, the message receiver module 300, at operation 320, opens a microphone (not shown) of the vehicle 10 to capture audio data of the environment outside the vehicle 10. Here, the message receiver module 300 may display, via the window 18, a graphic prompting and/or notifying the external user 80 that the microphone is open and recording audio.

In response to receiving audio data 302, at operation 330, the message receiver module 300 processes the audio data 302. For example, the microphone of the vehicle 10 may process the audio data 302 by filtering the audio data 302 and converting the audio data 302 from an analog signal to a digital signal. As the microphone processes the audio data 302, the message receiver module 300 may store the audio data 302 in a buffer of the memory hardware 14 of the vehicle for additional processing. In some implementations, the message receiver module 300 implements a wake-word process to determine whether the audio data 302 includes one or more words associated with leaving a message without performing speech recognition on the audio data 302. As used herein, one or more words associated with leaving a message may include, without limitation, urgent, please call me at, my insurance is, please text me at, please email me at, I'm sorry, it was an accident, etc. For example, the message receiver module 300 may detect acoustic features in the audio data 302 such as mel-frequency cepstral coefficients (MFCCs) that are representations of short-term power spectrums, or mel-scale filterbank energies, and compare the detected acoustic features in the audio data 302 to acoustic features stored in the message receiver module 300.

At operation 330, when the wake-word process determines that the audio data 302 includes the one or more words associated with leaving a message, the message receiver module 300 may trigger a speech recognizer to perform speech recognition or semantic interpretation on the audio data 302 to generate a transcription of the audio data 302. Thereafter, at operation 340, the message receiver module 300 may generate an external user message 304 based on the audio data 302 and the transcription of the audio data 302. For example, the message receiver module 300 may include an embedded model such as an embedded large language model (LLM) configured to receive the audio data 302 and the transcription of the audio data 302 as a prompt and generate, as output, an annotation of the urgency and/or priority of the external user message 304.

At operation 350, the message receiver module 300 may determine whether the priority of the external user message 304 exceeds a priority threshold of the vehicle 10. The priority threshold may be configurable by the user 102 and/or the manufacturer of the vehicle 10. For example, the priority threshold may filter out non-urgent external user messages 304 that do not exceed the priority threshold. Here, the message receiver module 300 may save the audio data 302 and/or transcription of the audio data 302 to replay for the user 102 when the user 102 returns to the vehicle 10. In implementations where the priority of the external user message 304 exceeds the priority threshold of the vehicle 10, at operation 360, the message receiver module 300 may transmit the external user message 304 to the user 102 for review. For example, if the external user message 304 is urgent, the message receiver module 300 may transmit the external user message 304 to the user device 70 of the user 102.

Figure 5A:
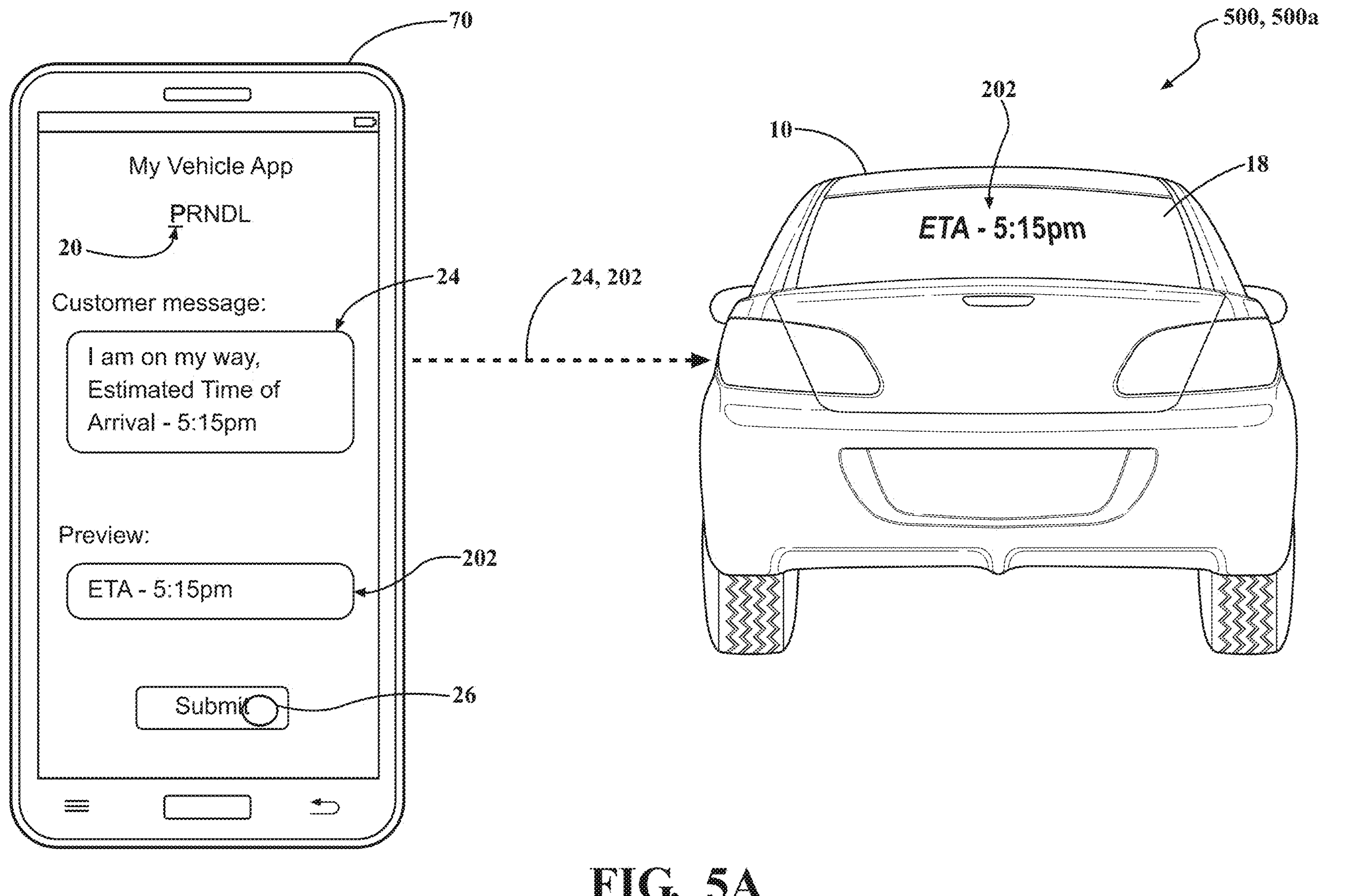
FIG. 5A is a schematic view of generating a message to communicate with an external user using the system of FIG. 1.
Figure 5B:
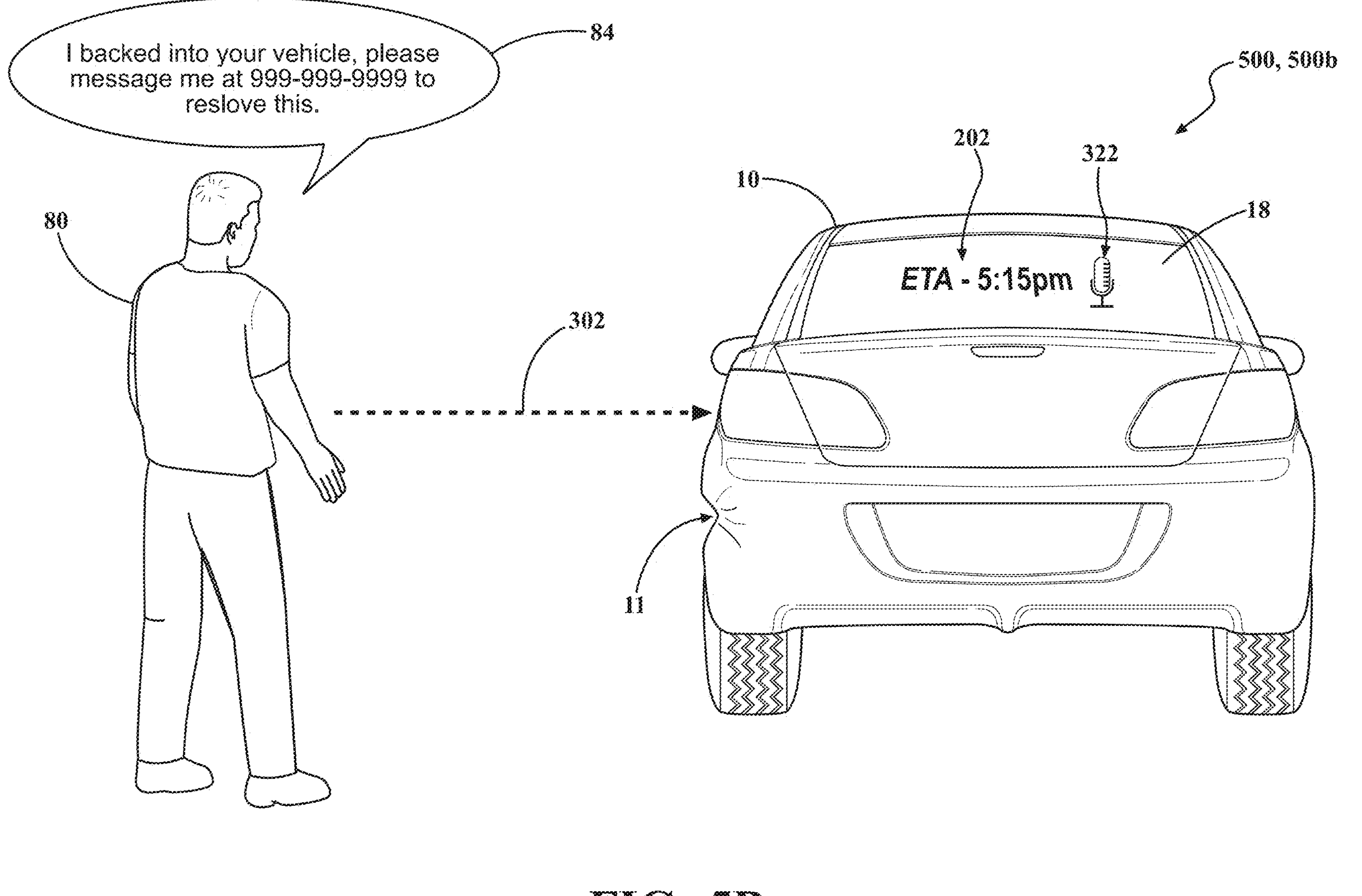
FIG. 5B is a schematic view of an external user leaving a message using the system of FIG. 1.

With reference to FIGS. 5A and 5B, example implementations 500*a*, 500*b* are shown, where the external communication system 110 executes the message generator module 200 (FIG. 5A) and the message receiver module 300 (FIG. 5B). In the examples shown, the vehicle 10 is parked and the user 102 is away from the vehicle 10. However, the user 102 is in communication with the vehicle 10 via the user device 70. For example, as noted above, an assistant application of the user device 70 facilitate communication between the user 102 and the external communication system 110 of the vehicle 10.

With particular reference to FIG. 5A, the external communication system 110 may display the assistant application on a screen of the user device 70. Here, the user device 70 shows that the detected status 20 of the vehicle 10 indicates that the vehicle 10 is parked. The user device 70 may further include a text box configured to capture a user-defined message 24 from the user 102. In the example, the user-defined message 24 includes "I am on my way. Estimated Time of Arrival—5:15 pm." In these examples, the message generator module 200 may re-format the user-defined message 24 to conform to parameters of the message 202. As shown the message generator module 200 may tokenize the user-defined message 24 to generate the message 202, and provide the user 102 with a preview of the message 202. In particular, the user device 70 displays "ETA—5:15 pm" in the preview window. Thereafter, the user may provide a user indication 26 indicating approval of the message 202 for display in the window 18 of the vehicle 10 by selecting a submit button displayed on the screen of the user device 70.

In response to the user indication 26 indicating approval of the message 202 for display in the window 18 of the vehicle 10, the user device 70 transmits the message 202 to the head-up display 16 of the vehicle 10, whereby the head-up display 16 displays the message 202 via the window 18. In particular, as shown, the window 18 shows the message 202 "ETA—5:15 pm" for external users 80 to view when passing the vehicle 10. Notably, this may provide helpful notice to external users 80 that may be seeking to use the parking space currently occupied by the vehicle 10.

With reference to FIG. 5B, an external user 80 is shown proximate to the vehicle 10, and the vehicle 10 includes recent damage 11 to its rear bumper. Here, the external user 80 may have recently backed into the vehicle 10, and needs to reach the user 102 of the vehicle 10 to relay insurance information. The vehicle 10 may detect, based on sensor data 82 received by the message receiver module 300, that the external user 80 is within the threshold distance of the vehicle 10. In response, the message receiver module 300 may prompt, via the window 18, the external user 80 to leave a message for the user 102 of the vehicle 10. As shown, the message receiver module 300 may prompt the external user 80 by displaying a microphone graphic 322 in the window 18, the microphone graphic 322 notifying the external user 80 that the vehicle microphone is open and recording audio data 302.

In response to the prompt (e.g., the microphone graphic 322), the external user 80 speaks an utterance 84 "I backed into your vehicle, please message me at 999-999-9999 to resolve this." The message receiver module 300 may receive the audio data 302 corresponding to the utterance 84 and generate an external user message 304 relaying the audio data 302, a transcription of the audio data 302 and/or annotations of the priority and content of the audio data 302. Based on the urgency of the external user message 304, the message receiver module 300 may transmit the external user message 304 to the user 102 (e.g., to the user device 70), or hold the external user message 304 locally at the vehicle 10 for playback to the user 102 when the user 102 returns to the vehicle 10. Advantageously, the message receiver module 300 eliminates the need for the external user 80 to obtain a pen and paper to leave a message for the user 102. Moreover, based on the urgency, the message receiver module 300 allows the external user message 304 to reach the user 102 faster than waiting for the user 102 to return to the vehicle 10.

Referring again to FIGS. 1 and 4, in some implementations, the external communication system 110 further monitors the health of the user 102 of the vehicle 10 via the driver monitoring module 400. For example, as shown in FIG. 1, the vehicle 10 may include a health monitoring system 50 that measures user data 52 (e.g., health data) of the user 102 of the vehicle 10. The driver monitoring module 400 is configured to receive the user data 52 as input and generate, as output, an emergency message 402 for display via the window 18 of the vehicle 10 when the user 102 is experiencing a medical emergency. As used herein, the user data 52 measured by the health monitoring system 50 may include one or more of pulse rate beats per minute of the user 102, the temperature of the user 102, the posture of the user 102, the oxygen levels of the user 102, or the eye movement of the user 102. The medical emergency may include a vascular or cerebral event such as epilepsy, seizure, collapse, stroke, or any other medical event that inhibits the user 102 from safely operating the vehicle 10. Notably, the driver monitoring module 400 operates independent of the status 20 of the vehicle and, as such, may detect a medical emergency whether the vehicle 10 is in park, reverse, neutral, drive, or low gear.

Figure 4:
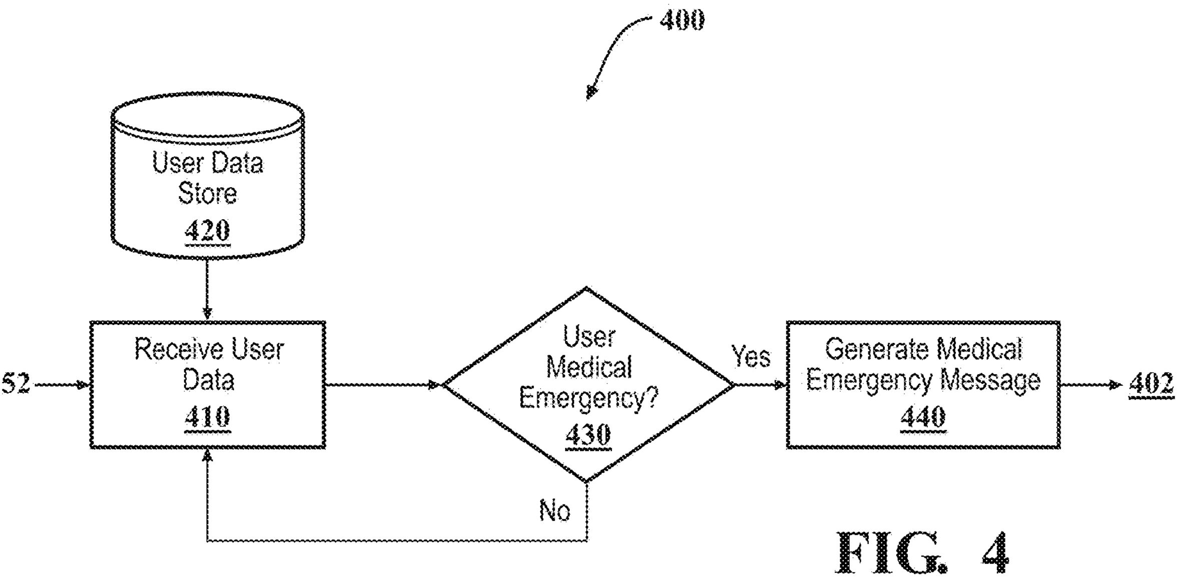
FIG. 4 is a driver monitoring module flowchart for the system of FIG. 1.

With particular reference to FIG. 4, the driver monitoring module 400, at operation 410, receives the user data 52 measured by the health monitoring system 50. At operation 430, the driver monitoring module 400 determines, based on the user data 52, whether the user is experiencing a medical emergency. In some implementations, the health monitoring module 400 has access to a user data store 420 that records/stores health records of the user 102. For example, the health records may include the existing health conditions of the user 102, the chronic health conditions of the user 102, the age of the user 102, the blood group of the user 102, and/or the in case of emergency (ICE) contact information for the user 102. Here, detecting that the user 102 is detecting the medical emergency may be further based on the health records of the user 102. For instance, the health records may confirm the findings based on the user data 52.

In response to detecting that the user 102 is experiencing the medical emergency, the driver monitoring module 400 may generate for output, at operation 440, an emergency message 402 communicating the medical emergency to external users 80 outside of the vehicle 10. The emergency message 402 (also referred to as the message 402) may be displayed via the window 18 of the vehicle 10 such that external users 80 are notified about the medical emergency that the user 102 is experiencing. By communicating the emergency message 402, emergency personnel may more quickly identify the vehicle 10 and/or the user 102 that requires assistance.

In some implementations, the driver monitoring module 400 performs, without input from the user 102, follow up operations to further minimize the impacts of the medical emergency. For example, the driver monitoring module 400 may generate instructions for the vehicle 10 to navigate (i.e., drive) to safety to prevent any collisions between the vehicle 10 and other objects. The driver monitoring module 400 may additionally or alternatively transmit the emergency message 402 to an emergency service to request assistance for the user 102.

Figure 6:
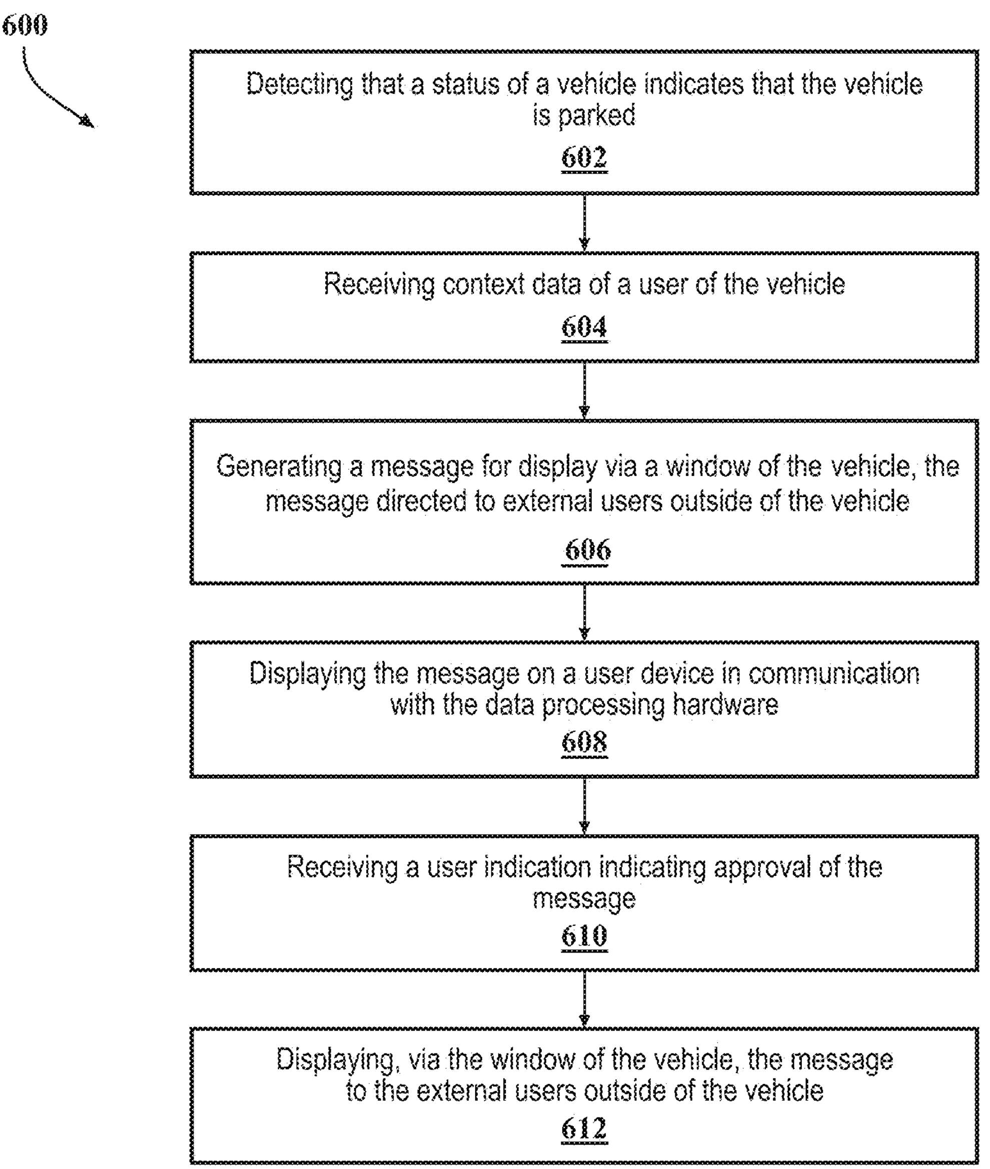
FIG. 6 is a flowchart of an example arrangement of operations for a method of leaving a message or communicating with someone outside of a vehicle.

FIG. 6 includes a flowchart of an example arrangement of operations for a method 600 of leaving a message or communicating with someone outside of a vehicle. The method 600 may be described with reference to FIGS. 1-5B. Data processing hardware (e.g., data processing hardware 12, 62, 72 of FIG. 1) may execute instructions stored on memory hardware (e.g., memory hardware 14, 64, 74 of FIG. 1) to perform the example arrangement of operations for the method 600.

At operation 602, the method 600 includes detecting that a status 20 of a vehicle 10 indicates that the vehicle 10 is parked. The method 600 also includes, at operation 604, receiving context data 22 of a user 102 of the vehicle 10. At operation 606, the method 600 also includes generating a message 202 for display via a window 18 of the vehicle 10. Here, the message 202 is directed to external users 80 outside of the vehicle 10.

The method 600 further includes, at operation 608, displaying the message on a user device in communication with the data processing hardware 12, 62, 72. At operation 610, the method 600 also includes, at operation 610, receiving a user indication 26 indicating approval of the message 202 for display via the window 18 of the vehicle 10. At operation 612, the method 600 further includes displaying, via the window 18 of the vehicle 10, the message 202 to the external users 80 outside of the vehicle 10.

Figure 7:
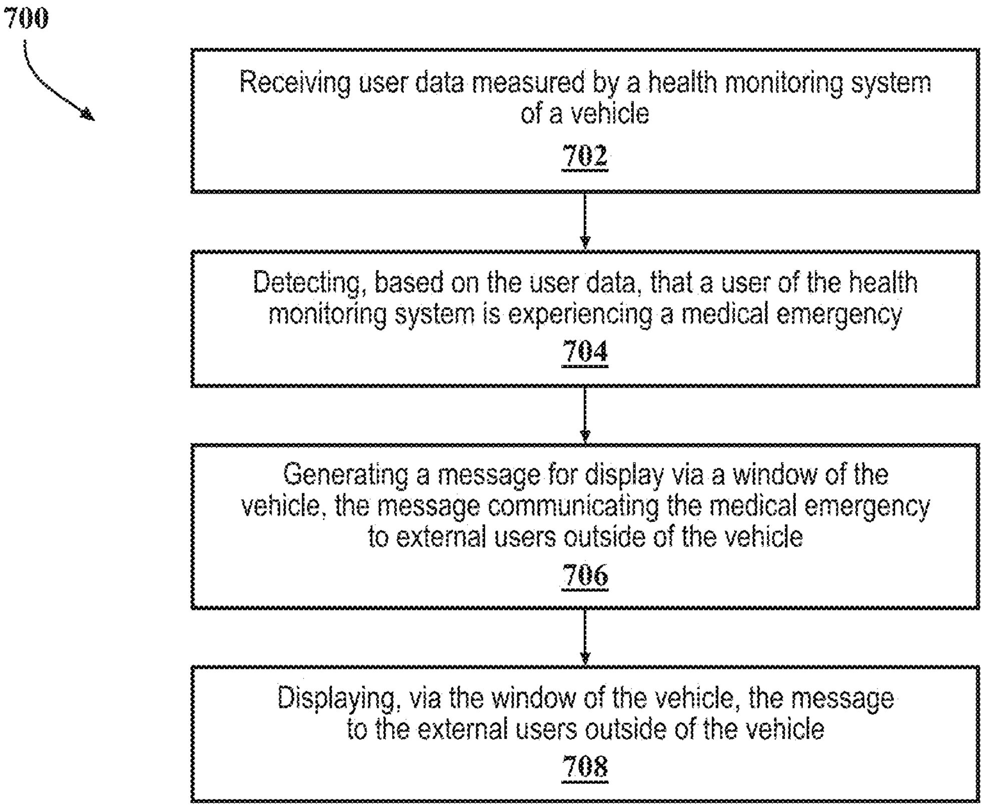
FIG. 7 is a flowchart of an example arrangement of operations for a method of communicating a medical emergency to someone outside of a vehicle.

FIG. 7 includes a flowchart of an example arrangement of operations for a method 700 of communicating a medical emergency to someone outside of a vehicle. The method 700 may be described with reference to FIGS. 1-5B. Data processing hardware (e.g., data processing hardware 12, 62, 72 of FIG. 1) may execute instructions stored on memory hardware (e.g., memory hardware 14, 64, 74 of FIG. 1) to perform the example arrangement of operations for the method 700.

At operation 702, the method 700 includes receiving user data 52 measured by a health monitoring system 50 of a vehicle 10. The method 700 also includes, at operation 704, detecting, based on the user data 52, that a user 102 of the vehicle 10 is experiencing a medical emergency. The method 700 further includes, at operation 706, generating a message 202 for display via a window 18 of the vehicle 10. Here, the message 202 communicates the medical emergency to external users 80 outside of the vehicle 10. At operation 708, the method 700 also includes displaying, via the window 18 of the vehicle 10, the message 202 to the external users 80 outside of the vehicle 10.

A number of implementations have been described. Nevertheless, it will be understood that various modifications may be made without departing from the spirit and scope of the disclosure. Accordingly, other implementations are within the scope of the following claims.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. A computer-implemented method when executed on data processing hardware causes the data processing hardware to perform operations comprising:

detecting that a status of a vehicle indicates that the vehicle is parked;

receiving context data of a user of the vehicle;

generating a message for display via a window of the vehicle, the message directed to external users outside of the vehicle;

transmitting, to a user device in communication with the data processing hardware, the message for display on the user device, wherein the user device is remote from the vehicle;

receiving a user indication indicating approval of the message for display via the window of the vehicle;

receiving a user-defined message from the user via the user device;

re-formatting the user-defined message for display via the window of the vehicle; and displaying, via the window of the vehicle, the re-formatted user-defined message to the external users outside of the vehicle.

2. The method of claim 1, wherein generating the message for display via the window comprises retrieving a predefined message from a message data store based on the context data of the user of the vehicle.

3. The method of claim 1, wherein the operations further comprise:

prompting the user to provide the user-defined message, wherein the user-defined message is received via a text box displayed on the user device.

4. The method of claim 3, wherein re-formatting the user-defined message for display via the window of the vehicle comprises tokenizing the user-defined message to generate the re-formatted user-defined message.

5. The method of claim 1, wherein the operations further comprise:

detecting that an external user is within a threshold distance of the vehicle;

prompting, via the window, the external user to leave a message for the user of the vehicle;

receiving audio data corresponding to an utterance spoken by the external user; and generating, based on the audio data, an external user message.

6. The method of claim 5, wherein the operations further comprise transmitting the external user message to the user of the vehicle.

7. The method of claim 1, wherein displaying, via the window of the vehicle, the message to the external users outside of the vehicle comprises projecting the message via a head-up display of the vehicle.

8. A computer-implemented method when executed on data processing hardware causes the data processing hardware to perform operations comprising:

receiving user data measured by a health monitoring system of a vehicle;

detecting, based on the user data, that a user of the vehicle is experiencing a medical emergency;

generating a message for display via a window of the vehicle, the message communicating the medical emergency to external users outside of the vehicle; and displaying, via the window of the vehicle, the message to the external users outside of the vehicle.

9. The method of claim 8, wherein the user data comprises one or more of:

pulse rate beats per minute;

temperature;

posture;

oxygen levels; or eye movement.

10. The method of claim 8, wherein detecting that the user of the vehicle is experiencing the medical emergency is further based on health records of the user.

11. The method of claim 8, wherein the operations further comprise:

instructing the vehicle to navigate to safety; and transmitting the message communicating the medical emergency to an emergency service.

12. A system comprising:

data processing hardware; and memory hardware in communication with the data processing hardware, the memory hardware storing instructions that when executed on the data processing hardware cause the data processing hardware to perform operations comprising:

detecting that a status of a vehicle indicates that the vehicle is parked;

receiving context data of a user of the vehicle;

generating a message for display via a window of the vehicle, the message directed to external users outside of the vehicle;

transmitting, to a user device in communication with the data processing hardware, the message for display on the user device, wherein the user device is remote from the vehicle;

receiving a user indication indicating approval of the message for display via the window of the vehicle;

receiving a user-defined message from the user via the user device;

re-formatting the user-defined message for display via the window of the vehicle; and displaying, via the window of the vehicle, the re-formatted user-defined message to the external users outside of the vehicle.

13. The system of claim 12, wherein generating the message for display via the window comprises retrieving a predefined message from a message data store based on the context data of the user of the vehicle.

14. The system of claim 12, wherein the operations further comprise:

prompting the user to provide the user-defined message, wherein the user-defined message is received via a text box displayed on the user device.

15. The system of claim 14, wherein re-formatting the user-defined message for display via the window of the vehicle comprises tokenizing the user-defined message to generate the re-formatted user-defined message.

16. The system of claim 12, wherein the operations further comprise:

detecting that an external user is within a threshold distance of the vehicle;

prompting, via the window, the external user to leave a message for the user of the vehicle;

receiving audio data corresponding to an utterance spoken by the external user; and generating, based on the audio data, an external user message.

17. The system of claim 16, wherein the operations further comprise transmitting the external user message to the user of the vehicle.

18. The system of claim 12, wherein displaying, via the window of the vehicle, the message to the external users outside of the vehicle comprises projecting the message via a head-up display of the vehicle.

19. The system of claim 12, wherein the operations further comprise:

receiving user data measured by a health monitoring system of the vehicle;

detecting, based on the user data, that the user of the vehicle is experiencing a medical emergency;

generating an emergency message for display via the window of the vehicle, the emergency message communicating the medical emergency to the external users outside of the vehicle; and displaying, via the window of the vehicle, the emergency message to the external users outside of the vehicle.

20. The system of claim 19, wherein detecting that the user of the vehicle is experiencing the medical emergency is further based on health records of the user.

* * * * *